US012610996B1

(12) United States Patent
Arsenault

(10) Patent No.: US 12,610,996 B1
(45) Date of Patent: Apr. 28, 2026

(54) COMBINATION STORAGE AND STERILIZATION DEVICE FOR FAUX EYELASHES

(71) Applicant: Mea Madamba Arsenault, Tacoma, WA (US)

(72) Inventor: Mea Madamba Arsenault, Tacoma, WA (US)

( * ) Notice: Subject to any disclaimer, the term of this patent is extended or adjusted under 35 U.S.C. 154(b) by 419 days.

(21) Appl. No.: 18/195,553

(22) Filed: May 10, 2023

Related U.S. Application Data

(63) Continuation-in-part of application No. 17/978,756, filed on Nov. 1, 2022, now abandoned, which is a continuation of application No. 16/596,308, filed on Oct. 8, 2019, now Pat. No. 11,484,077.

(51) Int. Cl.
| *A41G 5/02* | (2006.01) |
| *A45C 11/00* | (2006.01) |
| *A45C 15/04* | (2006.01) |
| *A61L 2/10* | (2006.01) |
| *A61L 2/24* | (2006.01) |
| *A61L 2/26* | (2006.01) |
| *A61L 103/05* | (2026.01) |

(52) U.S. Cl.
CPC ............. *A41G 5/02* (2013.01); *A45C 11/008* (2013.01); *A45C 15/04* (2013.01); *A61L 2/10* (2013.01); *A61L 2/24* (2013.01); *A61L 2/26* (2013.01); *A61L 2103/05* (2026.01); *A61L 2202/11* (2013.01); *A61L 2202/121* (2013.01); *A61L 2202/122* (2013.01); *A61L 2202/16* (2013.01)

(58) Field of Classification Search
CPC ......... A41G 5/02; A45C 11/008; A45C 15/04; A61L 2/10; A61L 2/24; A61L 2/26; A61L 2202/11; A61L 2202/16
See application file for complete search history.

(56) References Cited

U.S. PATENT DOCUMENTS

2013/0063922 A1* 3/2013 La Porte .................. A61L 2/10
250/455.11

FOREIGN PATENT DOCUMENTS

| FR | 2918854 A1 * | 1/2009 | ............ A45D 40/00 |
| KR | 101732108 B1 * | 5/2017 | ............ A45D 44/02 |
| KR | 101838571 B1 * | 3/2018 | ............ A45D 33/32 |

OTHER PUBLICATIONS

FR 2918854 A1 (Original/EnglishTranslation) (Year: 2009).*
KR 101838571 B1 (Original/EnglishTranslation) (Year: 2018).*
KR_101732108_B1 (English/OriginalTranslation) (Year: 2017).*

* cited by examiner

*Primary Examiner* — Maris R Kessel
*Assistant Examiner* — Nebyate Seged
(74) *Attorney, Agent, or Firm* — Richard Eldredge; Leavitt Eldredge Law Firm

(57) ABSTRACT

A combination storage and sterilization device for faux eyelashes is a portable device that stores and disinfects all types of faux eyelashes including eyelash extensions and eyelash tools. The device includes a casing, a cover, and a base. The device includes a sterilization cavity and a storage cavity. The device includes a light-up mechanism to indicate on going sterilization. The device includes a sterilization mechanism to sterilize the faux lashes and eyelash tools.

19 Claims, 12 Drawing Sheets

COMBINATION STORAGE AND STERILIZATION DEVICE FOR FAUX EYELASHES

CROSS REFERENCE TO RELATED APPLICATIONS

This application is a continuation in part of U.S. application Ser. No. 17/978,756, filed on Nov. 1, 2022 and a continuation of U.S. application Ser. No. U.S. Ser. No. 16/596,308 filed on Oct. 9, 2019, of which are hereby incorporated by reference in its entirety.

BACKGROUND

1. Field of the Invention

The present invention relates generally to cosmetic storage devices, and more specifically, to a combination storage and sterilization device for all types of faux eyelashes including eyelash extensions and eyelash tools.

2. Description of Related Art

Cosmetic storage devices are well known in the art and are effective means to store cosmetic products used for personal care.

One of the problems commonly associated with cosmetic storage devices is the lack of hygienic storage means. For example, faux eyelashes are prone to cause eye infections and dry eye syndrome in a user if not properly sterilized and hygienically stored.

Accordingly, although great strides have been made in the area of cosmetic storage devices, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
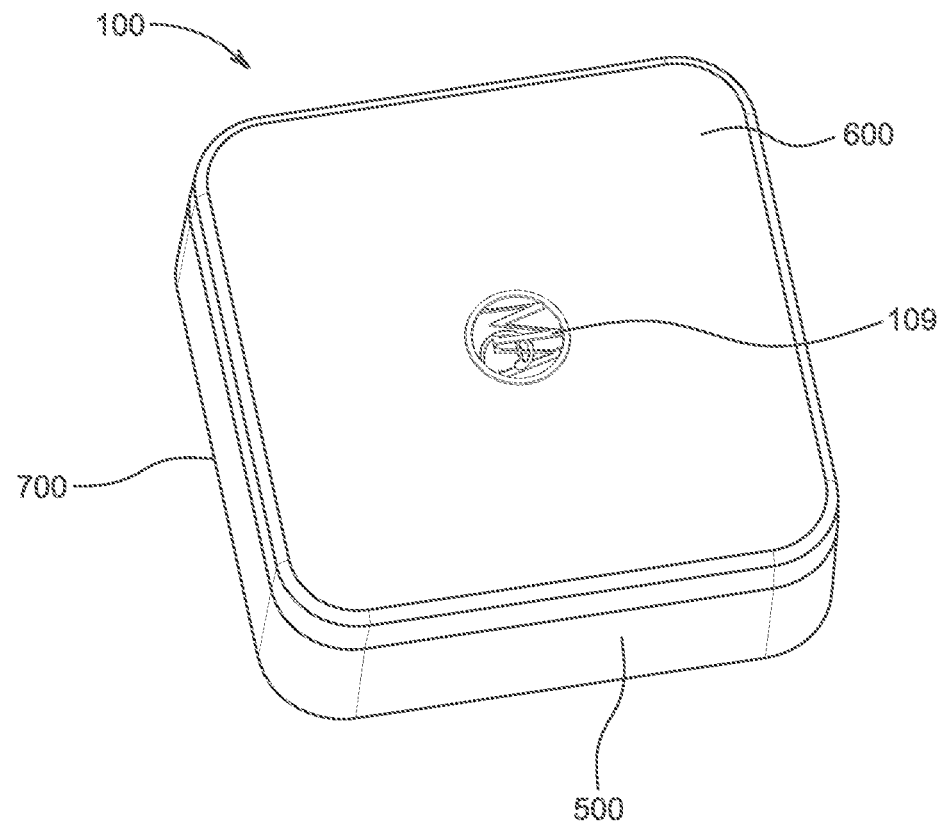
FIG. 1 is a perspective view of a combination storage and sterilization device for faux eyelashes and eyelash tools in accordance with a preferred embodiment of the present application.

While the device and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the device and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The device and method of use in accordance with the present application overcomes one or more of the above-discussed problems commonly associated with conventional cosmetic storage devices. Specifically, a user can both sterilize faux eyelashes and hygienically store the faux eyelashes for subsequent use. The device also allows for the sterilization of eyelash tools as well as allows for storage of said tools. The device lights up as a visual indicator during sterilization and collects and drains any water from the faux eyelashes or tools. These and other unique features of the device and method of use are discussed below and illustrated in the accompanying drawings.

The device and method of use will be understood, both as to its structure and operation, from the accompanying drawings, taken in conjunction with the accompanying description. Several embodiments of the device are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

Unless defined otherwise, faux eyelashes encompass all foreign eyelash types that are applied on or around one's natural lash and is made of material commonly understood by one of ordinary skill in the art to which this invention belongs, including but not limited to strip lashes, magnetic lashes, magnetic lash liner, eyelash extensions, that are made from mink, human hair, synthetic material, horse hair, other types of animal hair, etc. Any application of faux eyelashes, preferred methods, techniques, devices, and materials are described, although any methods, techniques, devices, or materials similar or equivalent to those described herein may be used in the practice or testing of the present invention. Structures described herein are to be understood also to refer to functional equivalents of such structures.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein reference characters identify corresponding or similar elements throughout the several views, FIG. 1 depicts a perspective view of a combination storage and sterilization device for faux eyelashes in accordance with a preferred embodiment of the present application. It will be appreciated that device 100 overcomes one or more of the above-listed problems commonly associated with conventional cosmetic storage devices.

Figure 2:
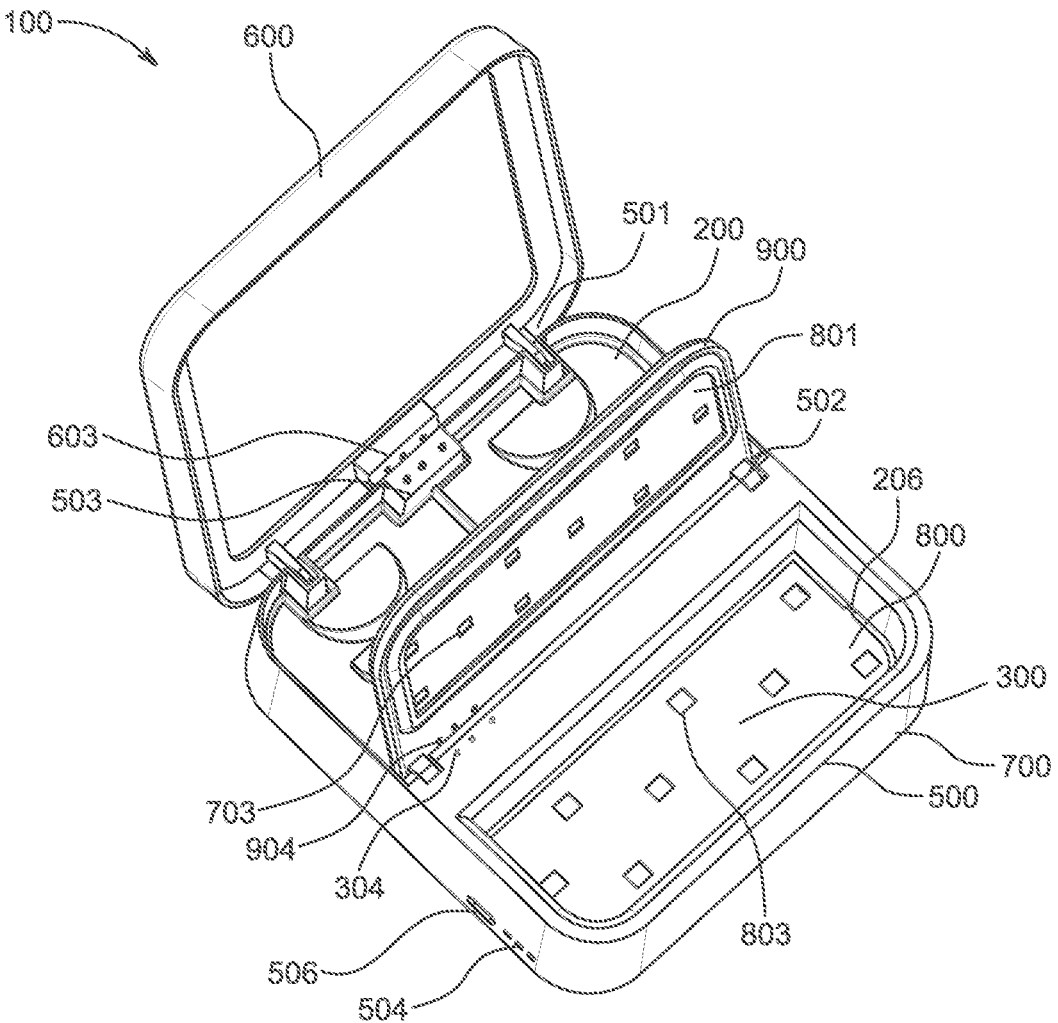
FIG. 2 is a perspective view of the device of FIG. 1 in a cover open configuration.
Figure 3:
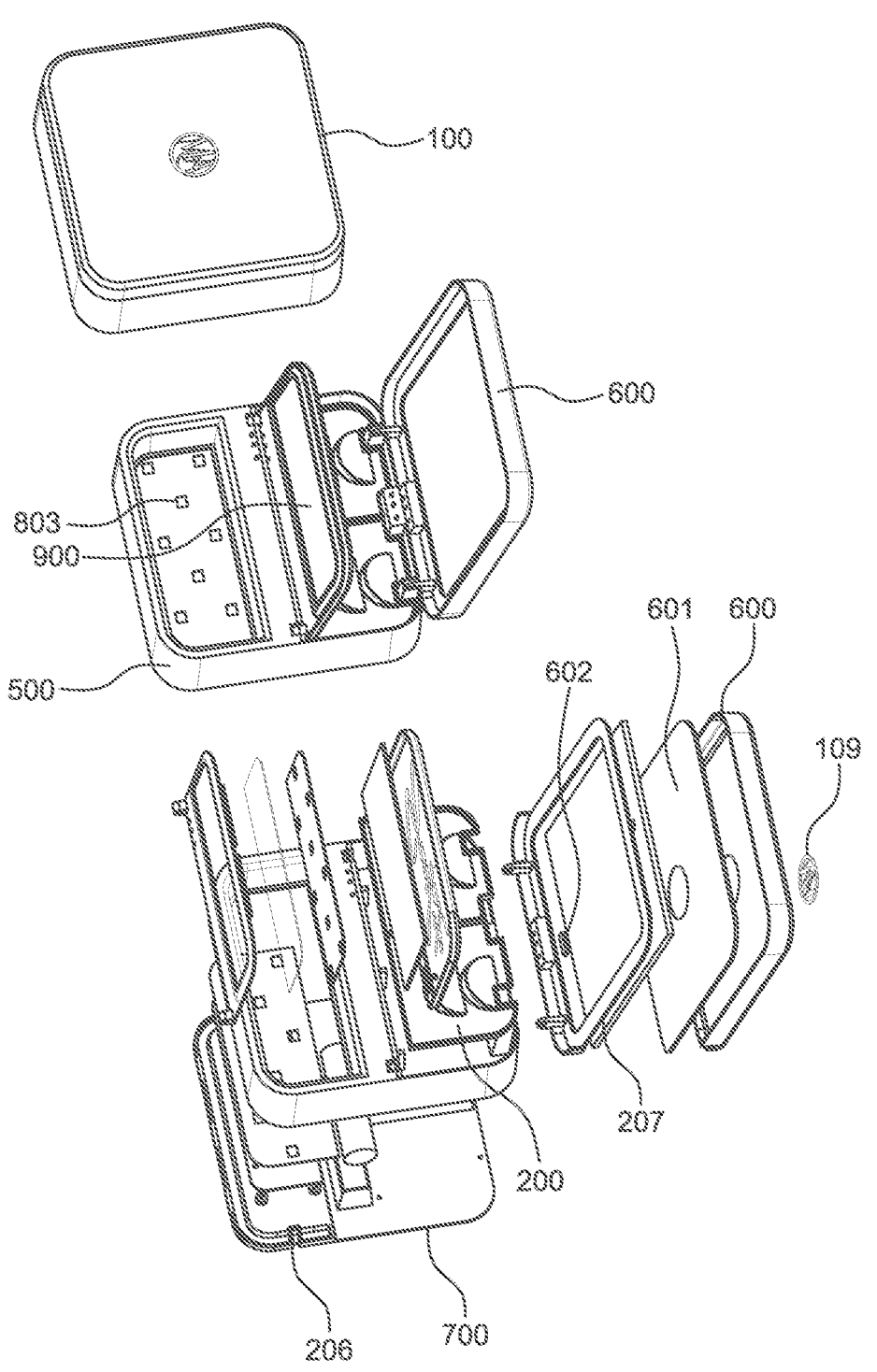
FIG. 3 is an exploded view of the device of FIG. 1 and FIG. 2 in a cover open configuration.

In the contemplated embodiment, as depicted in FIG. 2 and FIG. 3, device 100 includes a casing 500, a cover 600, and a base 700. The casing 500 includes a storage cavity 200 and a sterilization cavity 300. The sterilization cavity 300 includes a sterilization mechanism 800 and a sterilization cavity lid 900 which further includes a sterilization mechanism 801. The casing 500 and cover 600 are attached with a flexible hinge 501. The sterilization cavity 300 and sterilization cavity lid 900 are attached with a flexible hinge 502.

Figure 4:
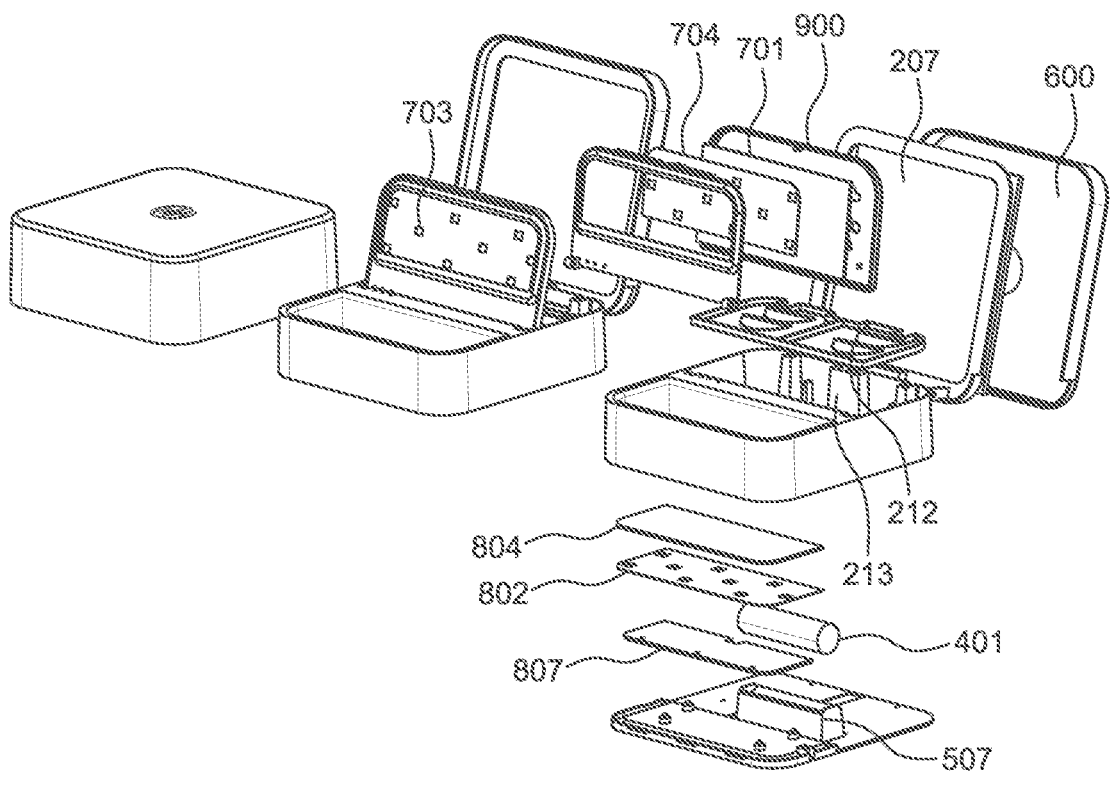
FIG. 4 is an exploded perspective view of the device in FIG. 2 in a cover open configuration.

It is also contemplated and will be appreciated that the storage cavity 200 is divided in to two compartments, the upper compartment 211 and the lower compartment 213 by a horizontal faux eye lash storage holder 212, as depicted in FIG. 4. The upper compartment 211 is configured to receive a plurality faux eye lashes and the lower compartment 213 is configured to receive the eye lash tools. The casing 500 may further include electrical connector mechanism 503, as depicted in FIG. 2, near the center of the flexible hinge 501.

Figure 5:
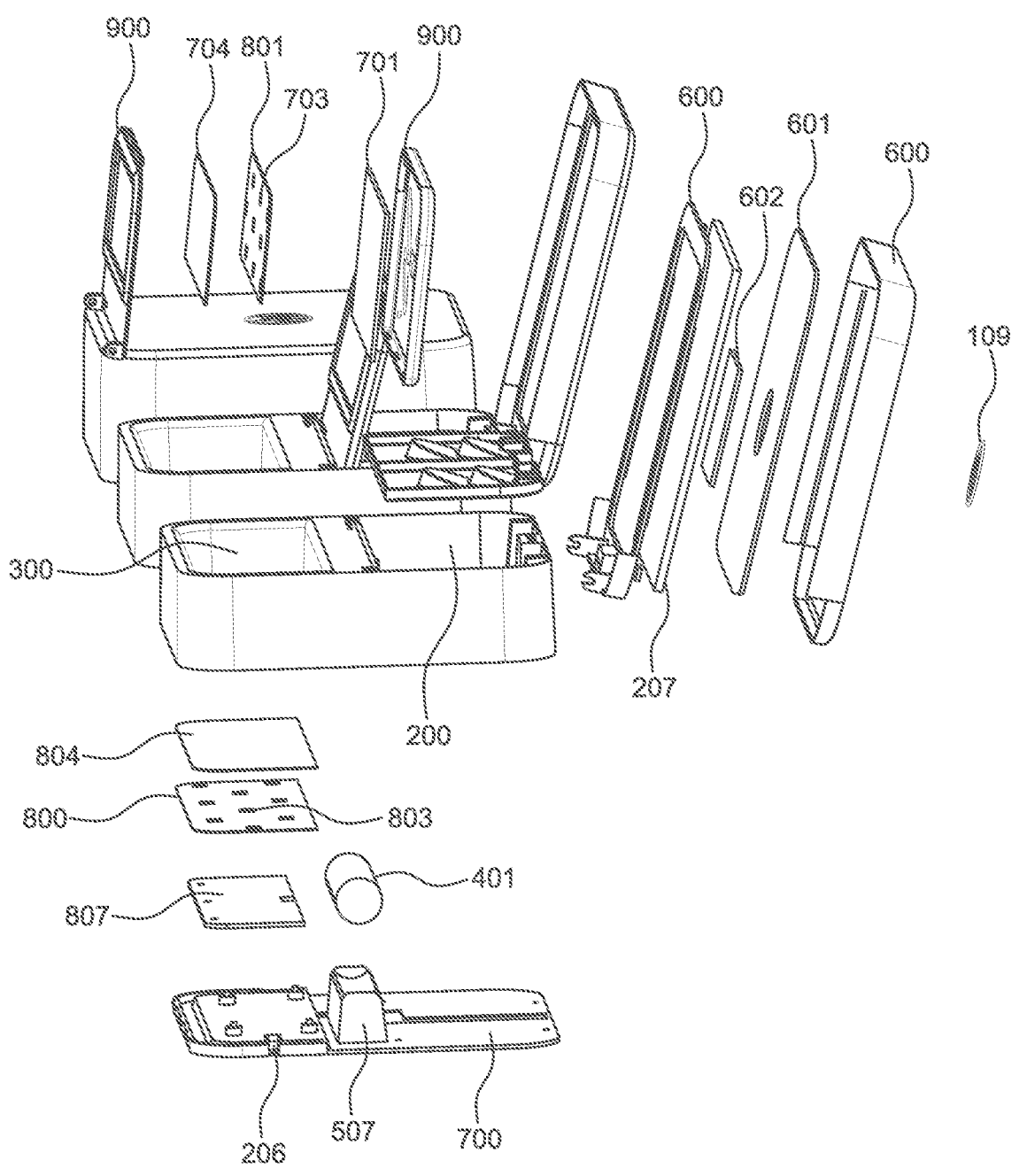
FIG. 5 is an exploded side view of the device in FIG. 2 in a cover open configuration.
Figure 11:
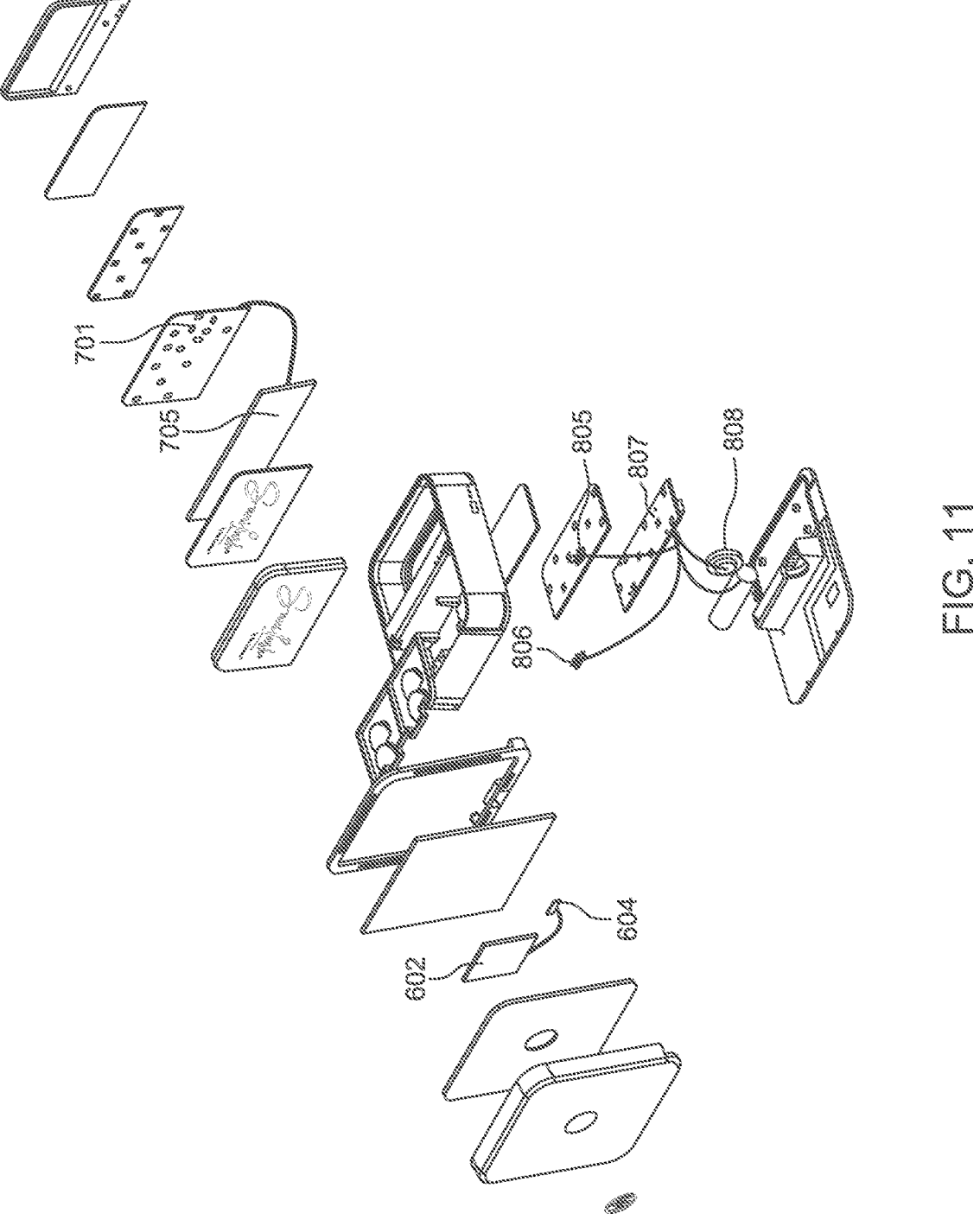
FIG. 11 is an exploded perspective view of the device in FIG. 2 in a cover open configuration depicting printed circuit boards.

As depicted in FIG. 4 and FIG. 5, the cover 600 may further include a black vinyl 601, a back light 602 and a PCB 604. The back light 602 may be embedded in the center of black vinyl 601 and is connected to PCB 604 as shown in FIG. 11. Black vinyl 601 blocks the back light from the other parts of the cover 600. The cover 600 may further include reflective mirror 207. The cover 600 may further include electrical connector mechanism 603, as depicted in FIG. 2.

The sterilization cavity 300 may include a sterilization mechanism 800 which further includes a printed circuit board (PCB) 807 on the base 700, a reflector 802, a clear protective sheath 804, and the sterilization cavity 300 further includes a printed circuit board (PCB) 805, and a printed circuit board (PCB) 806 as depicted in FIG. 5 and FIG. 11. The reflector 802 further includes a plurality of square-shaped openings 803. The reflector 802 facilitates disinfection by bouncing the radiation throughout the sterilization cavity 300, the disinfection happens with the printed circuit board (PCB) 807 holding the disinfection UV lights, which are exposed through square-shaped openings 803 of the reflector 802.

The sterilization cavity 300 may further include electrical connector mechanism 304 as depicted in FIG. 2. The sterilization cavity may further optionally comprise an audio device 808 as shown in FIG. 11 which gives sound signals in relation to the sterilization.

The sterilization cavity lid 900 may include a sterilization mechanism 801 which further includes a printed circuit board (PCB) 701, a reflector 702, a clear protective sheath 704, and a backlight 705 as depicted in FIG. 5 and FIG. 11. The reflector 702 further includes a plurality of square-shaped openings 703, as depicted in FIG. 5. The reflector 702 facilitates disinfection by bouncing the radiation throughout the sterilization cavity lid 900, the disinfection happens with the printed circuit board (PCB) 701 holding the disinfection UV lights, which are exposed through a plurality of square-shaped openings 703 of the reflector 702.

Figure 7:
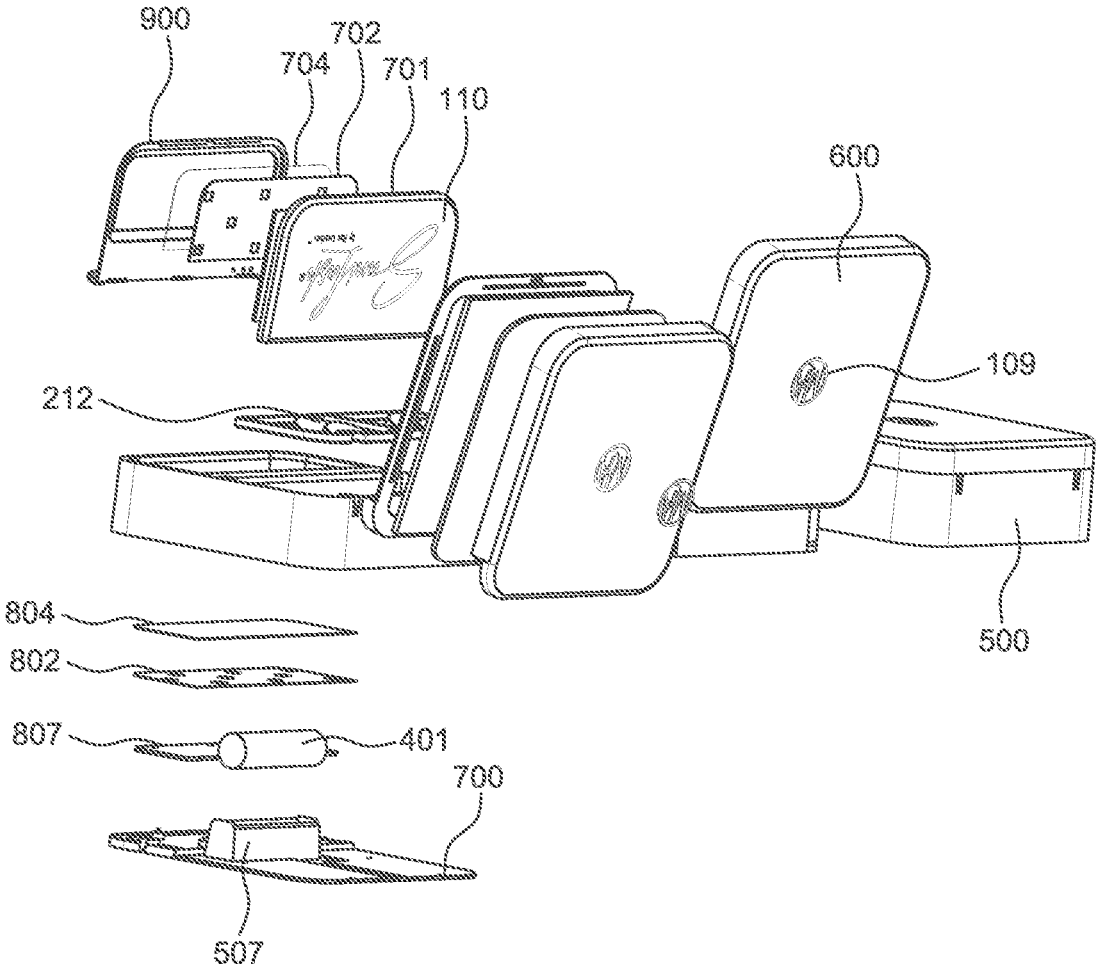
FIG. 7 is an exploded perspective view of the device in FIG. 2 in a cover open configuration.
Figure 9:
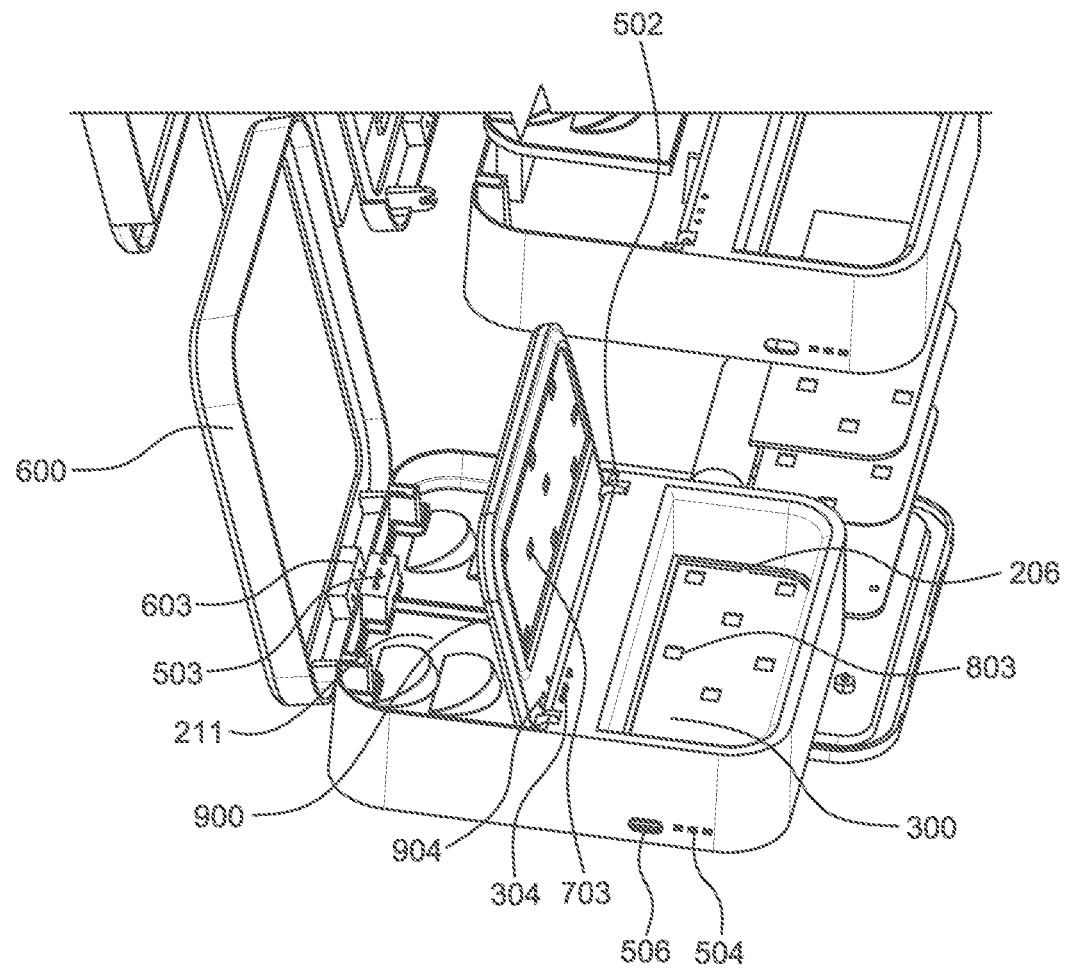
FIG. 9 is a perspective view of the device of FIG. 1 in a cover open configuration.
Figure 10:
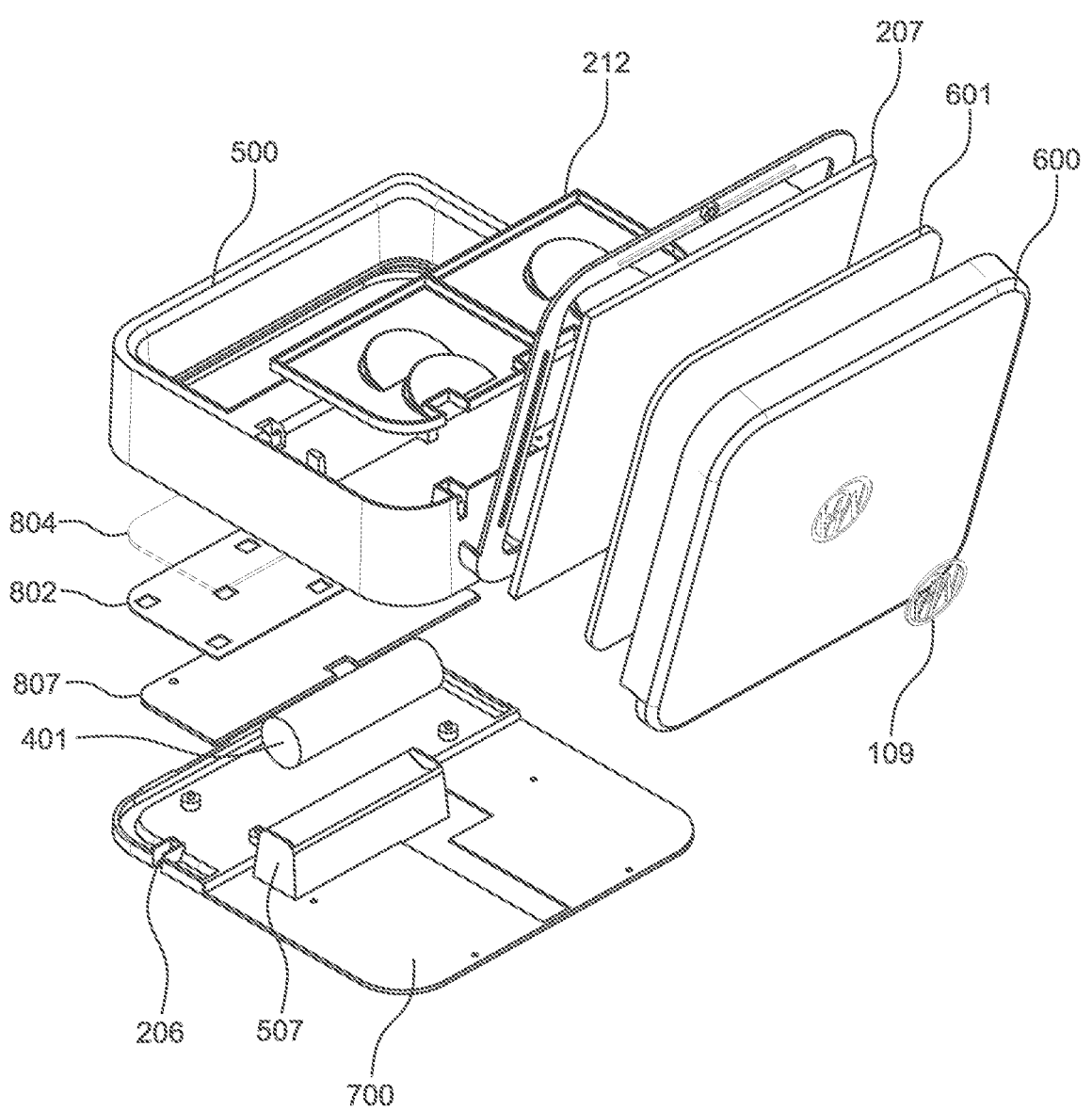
FIG. 10 is an exploded perspective view of the device in FIG. 2 in a cover open configuration.

The sterilization cavity lid 900 may further include electrical connector mechanism 904, as depicted in FIG. 2. The cover 600 may include a design 109 that lights up during sterilization when in the closed configuration, as depicted in FIG. 5. The sterilization cavity lid 900 may include a design 110 that lights up during sterilization when in the closed configuration, as depicted in FIG. 7. As in FIG. 9, the lighting up of the design on the cover 600 during sterilization and when in closed configuration is facilitated by completing the electrical connection path by contacting the electrical connector mechanism 503 of the casing 500 with the electrical connector mechanism 603 of the cover 600. The lighting up of the design on the sterilization cavity lid 900 during sterilization and when in closed configuration is facilitated by completing the electrical connection path by contacting the electrical connector mechanism 304 of the sterilization cavity 300 with the electrical connector mechanism 904 of the sterilization cavity lid 900.

Figure 6:
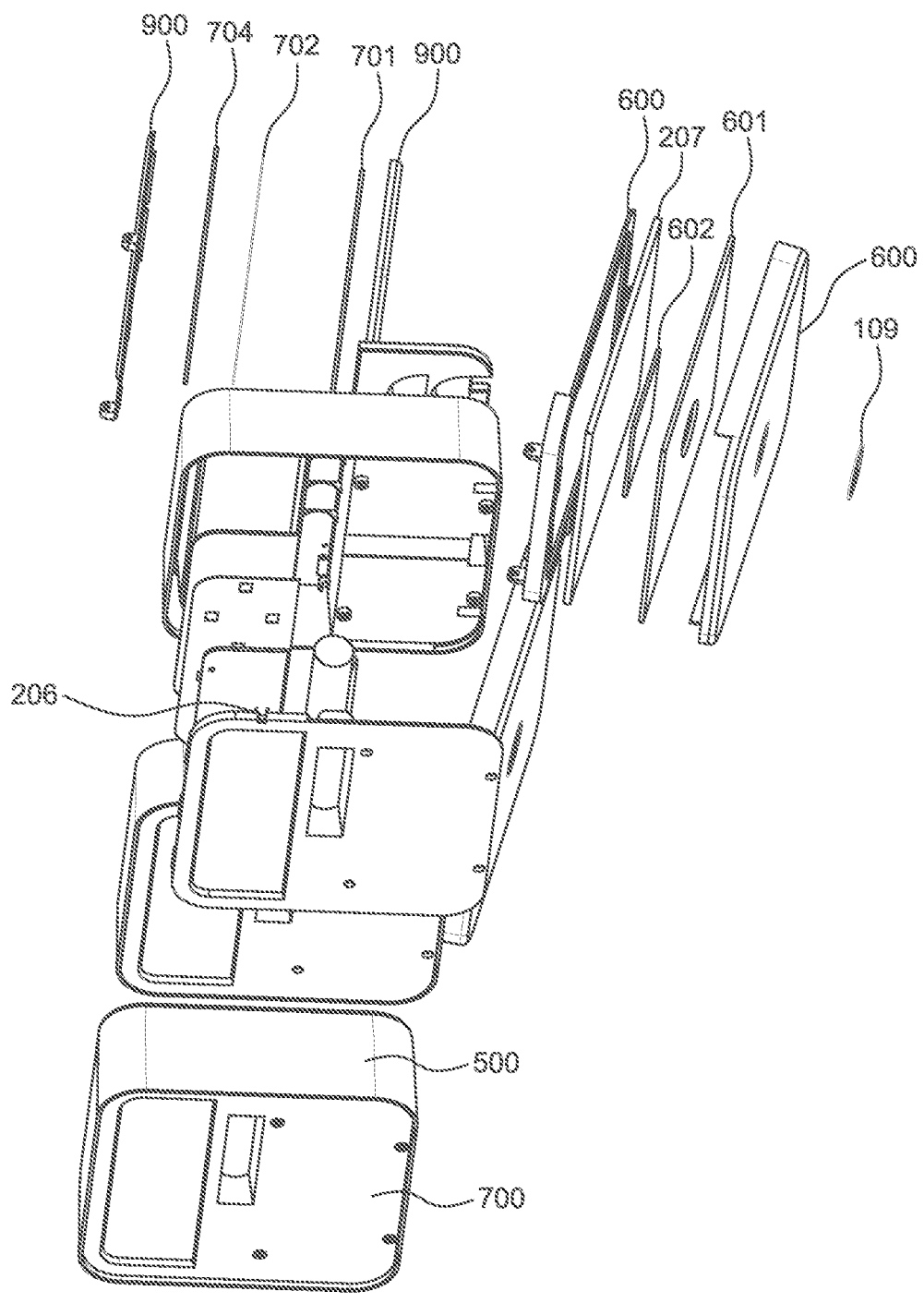
FIG. 6 is an exploded bottom view of the device in FIG. 2 in a cover open configuration.
Figure 8:
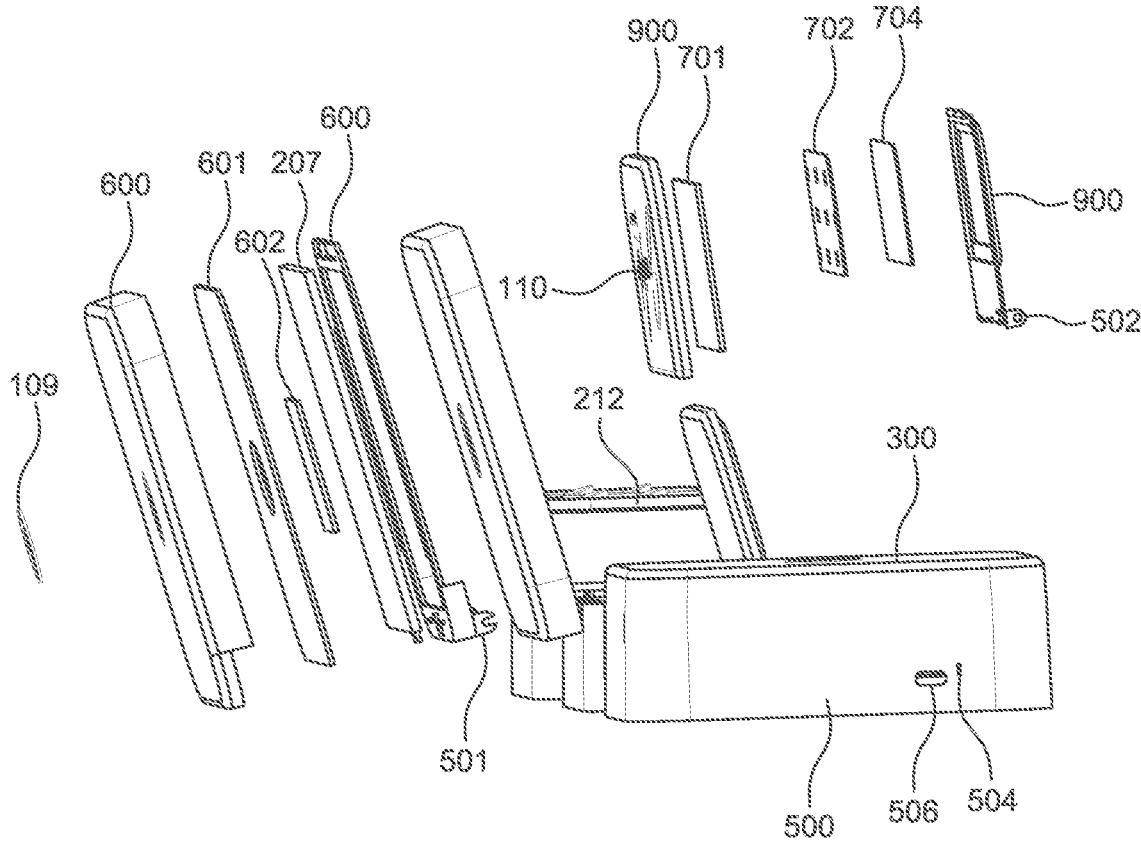
FIG. 8 is an exploded side view of the device in in FIG. 2 in a cover open configuration.

The device 100 may further include a sterilization cavity lid 900 connected to the sterilization cavity 300 allowing the sterilization cavity 300 to be sealed separately from the casing 500. The sterilization cavity lid 900 may light-up the design 110 during the sterilization, with the open configuration of the cover 600. When both the sterilization cavity lid 900 and cover 600 are in the closed configuration, the design 109 of the cover lights up during the sterilization. The device 100 is opaque on all sides and prevents the transmission of radiation outside of the device and prevents exposure of the user to the sterilization radiation. The device 100 provides a complete UV radiation barrier when the sterilization is going on in sterilization cavity 300 with sterilization cavity lid 900 in closed configuration completely preventing UV radiation exposure of the user making it absolutely safe to access the storage cavity 200. The device 100 completely shuts off the sterilization mechanism 800 and sterilization mechanism 801 upon opening the sterilization cavity lid 900, thereby preventing any kind of UV radiation exposure. The device 100 may further include a drip outlet 206 housed within the sterilization cavity 300, which would allow access to the base of the device 700, as depicted in FIG. 6. The casing 500 may further include a USB connecting port 506 and a battery life indicator 504 on the outer side of the casing 500, as depicted in FIG. 8. The base 700 may include a battery storage compartment 507, as depicted in FIG. 7.

The light up design of the present application including but not limited to a logo or a word or any sign that lights up when in closed configuration of the cover 600 and sterilization cavity lid 900 during the duration of sterilization, which in turn provides a visual indicator of ongoing sterilization once the power source is turned on. The electrical connector mechanism of the present application including but not limited to pogo pin or spring-loaded pin or any other suitable electrical connector mechanism.

Device 100 may further include a locking mechanism such as a magnetic latch or the like for securing the cover 600 over the casing 500 and for securing the sterilization cavity lid 900 over the sterilization cavity 300. The cover 600 may also include a reflective mirror 207 allowing the user to apply the faux eyelashes without the need for a separate mirror. As depicted in FIG. 2, the sterilization mechanism 800 is housed within the sterilization cavity 300 and the sterilization mechanism 801 is housed within the sterilization cavity lid 900. The sterilization mechanisms 800 and 801 may include a UV light source or any other suitable sterilization source. The base 700 has a battery storage compartment 507 which may in turn receive one or more batteries. The device 100 may also include a power source 401 to provide power to the sterilization mechanism 800 and sterilization mechanism 801. The power source 401 may be one or more batteries or plugged directly into a socket or a combination.

The device 100 may also include a drip outlet 206 at the bottom of the device 100 or a similar drainage system for assisting in the evaporation and drainage of water droplets that passed outside through the drip outlet 206 which is enclosed in the casing 500. The elevated edge of the base 700 assists with the drainage system raising the device 100 so as not to sit flush on any flat surface thereby keeping the drip outlet 206 exposed.

Figure 12:
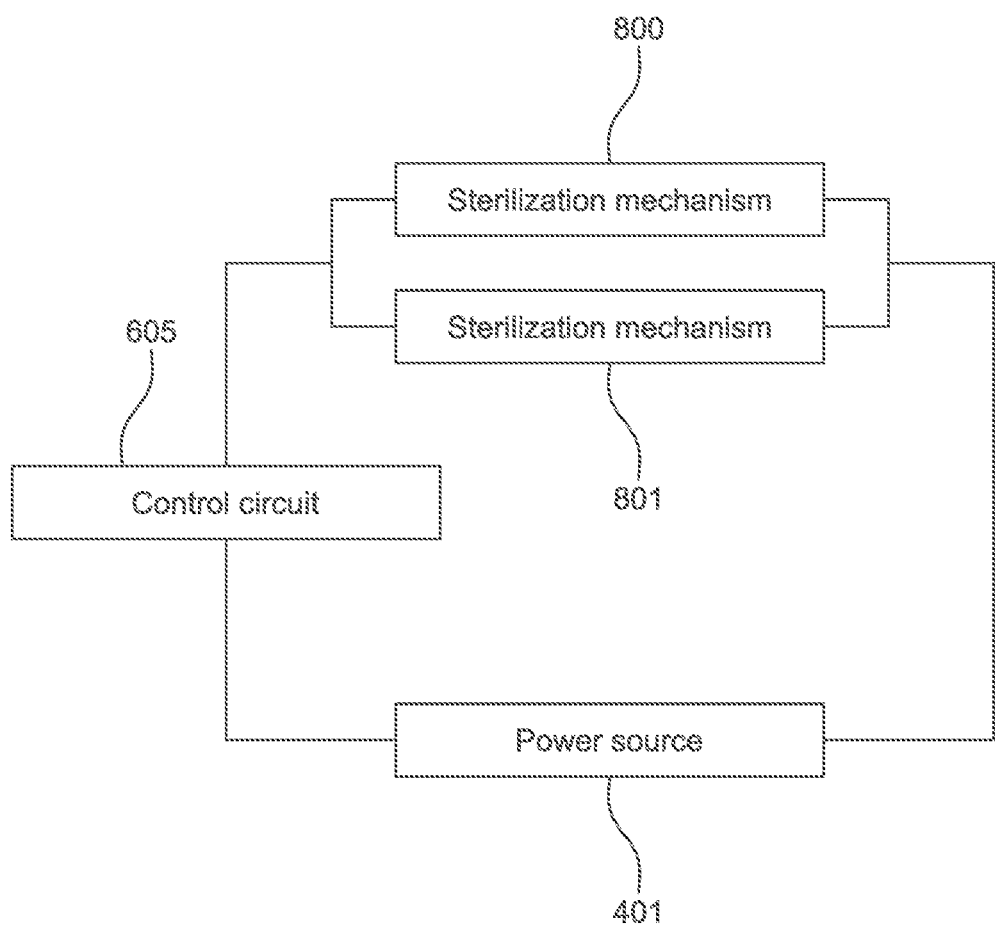
FIG. 12 is a schematic of sterilization mechanisms connected to a control circuit and a power source.

The device 100 may further include a control circuit 605 connected to the sterilization mechanism 800 and sterilization mechanism 801 and the power source 401 as shown in FIG. 12. The control circuit 605 may further comprise a timer and an inverter and is configured to automatically turn on and off the sterilization mechanism 800 and sterilization mechanism 801.

It should be appreciated that one of the unique features believed characteristic of the present application is the combination of storage and a sterilization mechanism for faux eyelashes as well as faux eyelash tools into a single device.

The device 100 may be compact making it easy for the user to carry around while traveling. The device 100 may also be a larger container that is mobile such as on wheels and may be useful for larger events such as for a makeup artist or a wedding party or the like. The device 100 may also have different configurations allowing for the sterilization of a plurality of faux eyelashes and/or eyelash tools in combination, as well as storing a plurality of additional faux eyelashes and eyelash tools and supplies. The device 100 may also be stationarily incorporated into furnishings or intended to sit atop a shelf.

It should also be appreciated that one of the unique features believed characteristic of the present application is that it provides a visual indicator by lighting up the cover or sterilization cavity lid during sterilization, and the whole device is compact and opaque and does not transmit any radiation outside, and thus making it easy and safe to use for sterilization of faux eyelashes and eyelash tools. The device of the present invention is aesthetically pleasing, fashionable, and portable for storing and sterilization of faux eyelashes and eyelash tools.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A combination storage and sterilization device for faux eyelashes and faux eyelash tools, comprising:
    a casing, having:
        a storage cavity;
        a sterilization cavity, the sterilization cavity is configured to receive and store a faux eyelash and configured to sterilize the faux eyelash;
    a cover secured to the casing; and
    a base;
    wherein the casing is attached to the base on the bottom and to the cover on the top;
    wherein the sterilization cavity is configured to include a sterilization mechanism and a sterilization cavity lid;
    wherein the casing is attached to the cover enabling a cover open configuration and a cover close configuration;
    wherein the sterilization cavity lid is attached to the sterilization cavity enabling a lid open configuration and a lid close configuration;
    wherein the storage cavity is configured to store faux eyelashes and eyelash tools; and
    wherein the cover further comprises a black vinyl, a back light, a printed circuit board, a reflective mirror and an electric connector mechanism.

2. The combination storage and sterilization device of claim 1, further comprising plurality of storage compartments configured to store faux eyelashes and eyelash tools.

3. The combination storage and sterilization device of claim 1, further comprising a power source connected to the sterilization mechanism and configured to provide power to the sterilization mechanism.

4. The combination storage and sterilization device of claim 3, wherein the power source is one or more of batteries.

5. The combination storage and sterilization device of claim 3, wherein the power source is provided by plugging the device directly into a socket.

6. The combination storage and sterilization device of claim 3, further comprising a circuit connected to the sterilization mechanism and the power source, the circuit having a timer and an inverter and configured to automatically turn on and off the sterilization mechanism.

7. The combination storage and sterilization device of claim 1, further comprising one or more designs on the cover configured to light-up when in cover closed configuration and connected to power source during sterilization.

8. The combination storage and sterilization device of claim 1, further comprising one or more designs on the sterilization cavity lid configured to light-up when in lid closed configuration and connected to power source during sterilization.

9. The combination storage and sterilization device of claim 1, wherein the casing further comprises an electrical connector mechanism.

10. The combination storage and sterilization device of claim 1, wherein the sterilization mechanism further comprises a plurality of printed circuit boards on the base, a reflector, and a clear protective sheath.

11. The combination storage and sterilization device of claim 10, further comprises square shaped openings in reflector.

12. The combination storage and sterilization device of claim 1, wherein the sterilization cavity further comprises an electrical connector mechanism.

13. The combination storage and sterilization device of claim 1, wherein the sterilization cavity lid further comprises a backlight, a printed circuit board, a reflector, a clear protective sheath and an electrical connector mechanism.

14. The combination storage and sterilization device of claim 1, further comprising a drip outlet configured to assist with evaporation and water drainage.

15. The combination storage and sterilization device of claim 1, further comprising a USB port and a battery life indicator.

16. The combination storage and sterilization device of claim 1, further comprising a locking mechanism configured to secure the cover in the cover closed configuration.

17. The combination storage and sterilization device of claim 1, further comprising a locking mechanism configured to secure the sterilization cavity lid in the lid closed configuration.

18. The combination storage and sterilization device of claim 1, wherein the device is configured to be opaque.

19. The combination storage and sterilization device of claim 1, wherein the sterilization cavity is configured to be opaque.

* * * * *